United States Patent [19]

Andon et al.

[11] Patent Number: 5,571,441
[45] Date of Patent: Nov. 5, 1996

[54] NUTRIENT SUPPLEMENT COMPOSITIONS PROVIDING PHYSIOLOGIC FEEDBACK

[75] Inventors: Mark B. Andon, Fairfield; Paul D. Leis, Jr., Hamilton, both of Ohio

[73] Assignee: The Procter & Gamble Company, Cincinnati, Ohio

[21] Appl. No.: 332,689

[22] Filed: Nov. 1, 1994

[51] Int. Cl.$^6$ .............................. A61K 47/00; A23L 1/30
[52] U.S. Cl. ................. 252/1; 424/439; 426/648
[58] Field of Search ................ 424/439; 252/1; 426/648

[56] References Cited

U.S. PATENT DOCUMENTS

| | | | |
|---|---|---|---|
| 4,070,488 | 1/1978 | Davis | 426/72 |
| 4,107,346 | 8/1978 | Kravitz | 426/648 |
| 4,214,996 | 7/1980 | Buddemeyer et al. | 252/1 |
| 4,454,162 | 6/1984 | Schanze | 426/74 |
| 4,725,427 | 2/1988 | Ashmead et al. | 424/44 |
| 4,935,256 | 6/1990 | Tsai | 426/330.3 |
| 5,035,888 | 7/1991 | Hara | 424/195.1 |

FOREIGN PATENT DOCUMENTS

| | | | |
|---|---|---|---|
| 472428A2 | 2/1992 | European Pat. Off. | A61K 9/68 |
| 2586532 | 9/1993 | France | A23L 1/36 |
| 3821385 | 1/1990 | Germany | A23F 3/32 |
| 5-336924 | 12/1993 | Japan | A23L 1/304 |
| 66014 | 7/1978 | Romania | A61K 9/20 |
| 91-044385 | 3/1989 | South Africa . | |

OTHER PUBLICATIONS

CA. 87:166282 1976.

Primary Examiner—Paul J. Killos
Attorney, Agent, or Firm—R. A. Dabek; J. C. Rasser

[57] ABSTRACT

The present invention is directed to novel nutritional supplement compositions providing physiologic feedback. The compositions comprise vitamins, minerals and central nervous system bracers. Flavanols can also be included in the composition. These compositions are useful in promoting regular consumption of nutritional supplements used for improving the diet.

The vitamin and mineral supplement can additionally comprise sweeteners, flavors, pharmaceutically acceptable carriers and excipients. The supplements can contain both vitamins and minerals.

24 Claims, No Drawings

NUTRIENT SUPPLEMENT COMPOSITIONS PROVIDING PHYSIOLOGIC FEEDBACK

TECHNICAL FIELD

The present invention is directed to novel nutritional supplement compositions providing physiologic feedback. The compositions comprise vitamins, minerals and central nervous system bracers. Flavanols can also be included in the composition. These compositions are useful in promoting regular consumption of nutritional supplements used for improving the diet.

BACKGROUND OF INVENTION

Vitamin and mineral supplements for human and veterinary use are commonplace. Nutrient intake surveys have shown large segments of the world's population consumes substantially less than the recommended amounts of numerous vitamins and minerals. For example, in the U.S.A. 60% or more of females age 20–29 years consume less than the recommended dietary allowance of vitamins A, E, B-6, folic acid, and the minerals calcium, magnesium, iron, and zinc. It is generally known that some diets, heavy physical exercise and disease conditions may require the intake of considerable quantities of vitamins and minerals apart from those generally available from what is considered a normal diet. Nutritional supplements are primarily important for those who have inadequate diets, however, individuals with a reduced ability to utilize or absorb vitamins and minerals from food, e.g., the elderly, also need nutritional supplementation.

Commercially available vitamin and mineral supplements are convenient and useful in many circumstances where improved nutrient uptake is desirable. However, adhering to a daily routine of nutritional supplementation has had limited success. For example, daily supplementation requires a change in normal habits and practices of the user. Further, some individuals find that supplements provide no immediate physiological signal to help them perceive a benefit or to establish a consistent routine of use. A number of other pharmacologic agents taken for health are typically associated with a noticeable bodily or physiological response. It is believed that the lack of a physiological signal limits the overall acceptability of nutritional supplements which is unfortunate since there is a need for supplementation to augment the daily intake of vitamins and minerals from foods.

A physiological signal that many people are accustomed to is the alertness response received by food-type tonics or bracers, such as caffeine. These materials can be useful for creating a perceived benefit and for establishing more regular use of nutritional supplements. These natural bracers, and in particular, the xanthine alkaloids (methylxanthines) are found in various plants. The methylxanthines are obtained by extraction of plants (e.g. coffee beans, cola nuts, tea plants). Plants containing methylxanthines are known to those skilled in the art. Preferred methylxanthines are 1, 3, 7-trimethylxanthine (caffeine), 1, 3-dimethylxanthine (theophylline) and 3, 7-dimethylxanthine (theobromine). Many people establish a consistent pattern of caffeine use due to its well documented effects as a tonic. One or more caffeine containing food or beverages-cocoa, chocolate, coffee, tea, soft drinks—are consumed daily by most adults and children. Cocoa and chocolate contain only small amounts of caffeine and are not usually consumed for the same reason as coffee, tea, and soft drinks.

Although it is clear that many people consume caffeine and other related tonics, there are well recognized problems with the usual caffeine containing foods. Caffeienated coffee is consumed by many people in the morning. Coffee is known to stimulate the gastric mucosa and increase stomach acid secretions which contributes to heart burn and irritation of ulcers. Coffee is also bitter tasting, so some people consume caffeine in the form of soft drinks. The high acid content of soft drinks, phosphoric for colas and "pepper" type soft drinks and citric acid for fruit flavored type beverages is well documented to etch or erode the enamel of the tooth surface. In addition, cola and "pepper" type soft drinks contributed greatly to the total phosphorus intake of the diet which imbalances the calcium to phosphorus ratio and can cause a negative effect on bone metabolism. Tea is another widely consumed source of caffeine but it also has some negatives associated with it. Tea contains anti-thiamin factors which stress the thiamin stores in the body and can lead to poor thiamin nutritional status. In addition, teas are often consumed with lemon and/or sugar. The lemon can increase the risk of dental erosion due to etching of the teeth from the high citric acid content and the sugar can provide a source of fermentable carbohydrate to the oral bacteria which increases the risk of caries. Apart from the negative effect of caffeine containing beverages, many people look for alternative ways to provide alertness benefits.

It would be desirable to provide the sought after bracing effects of caffeine or other similar ingredients in a composition which eliminates the negative effects of normal caffeine source carriers and yet provide a convenient and effective composition for promoting good health.

Thus, an object of the current invention is to provide compositions of vitamins and/or minerals and a central nervous system tonic in a convenient dose form. These compositions would provide vitamin and mineral supplements with a noticeable physiologic response and also the desired alertness effects without the negative components associated with typical caffeine containing beverages.

Some people avoid caffeine due to health reasons, i.e. the effect of caffeine on elevating blood pressure. It would be desirable, therefore, to have additional nutritional supplements which provide a physiological signal other than those of methylxanthines. Green tea is believed to have a relaxing benefit owing to the presence of flavanols (i.e., the catechins and epicatechins). Green tea has had several physiologic benefits attributed to it. It is believed to lower blood pressure and have other soothing and healing effects. These benefits have been attributed to flavanols. Black tea contains polymerized flavanols which do not impart the same degree of benefits of catechins and epicatechins.

Compositions comprising vitamins and/or minerals and flavanols would be useful as a convenient dose form for improving the diet while also providing a physiologic response and combined benefits of flavanols with those of vitamins and minerals to yield a more comprehensive product for the promotion of health.

It is further recognized that certain individuals seek the benefits of caffeine or similar ingredients but, closely control the amount of caffeine they ingest due to sensitivity to caffeine or because of caffeines undesirable effects (i.e. the promotion of nervousness). For some people, the negative effects of caffeine may eventually outweigh the positive so that caffeine is avoided altogether. Tea contains caffeine. However, the caffeine in tea does not appear to be as physiologically available due to the presence of flavanols. It is well known that the flavanols, in particular the unoxidized flavanols, present in green tea, help to control the negative effects of caffeine. See, for example, French patent No. 2,586,532 issued to Balansard et al.

Vitamin and mineral supplements having unique compositions containing a bracer, such as caffeine, along with the beneficial effects of flavanols or green tea would be useful for improving nutritional status and providing positive alertness benefits while limiting the negative effects.

Both caffeine and flavanol containing products are primarily consumed in the morning to obtain an alertness effect. Typically vitamins and minerals are also consumed in the morning. It would be more convenient if the nutritional supplements, methylxanthines and flavanols could be administered conjointly in a form which would provide nutritional supplementation and alertness without negative effects. These nutrient supplement compositions would be useful in providing a physiologically positive alertness benefit while providing feedback beneficial in establishing more regular use of a supplement.

The use of methylxanthines and/or flavanols are known in pharmaceutical and therapeutic preparations. The methylxanthines have primarily been used to treat various problems such as asthma, abdominal complications, and migraine headaches. However methylxanthines and in particular, caffeine, is used to counteract the adverse effects (i.e. drowsiness) caused by other ingredients in the pharmaceutical preparation. The flavanols, have been used for centuries to combat numerous diseases and illnesses, both real and imaginary.

While the beneficial effects of methylxanthines and flavanols, in particular caffeine and green tea, are suggested by the literature, the use of these materials in conjunction with vitamin and mineral supplements or the coadministering of the materials with vitamins and minerals in a convenient form is not known.

It would be desirable, therefore, to have vitamin and mineral supplements containing flavanols and methylxanthines or flavanols alone wherein physiological feedback is achieved.

It is an object of this invention to provide nutritional supplements which provide the physiologically positive alertness effects of a bracer along with the beneficial effects of the flavanols or green tea solids.

Another object of this invention is to provide a composition which reduces a multistep morning ritual for many people into a single convenient dose form.

It is further an object of this invention to provide vitamin i and mineral supplements which when taken, help to establish consistent use of the supplements.

These and other objects will become apparent from the description herein.

All percentages are by weight per unit dose unless otherwise indicated.

SUMMARY OF INVENTION

A vitamin and mineral supplement comprising:
(a) from about 3% to about 500% of the RDA of minerals; or from about 3% to about 1000% of the RDA of vitamins;
(b) from about 10 mg to about 4000 mg flavanols; and
(c) optionally, a bracer wherein said bracer delivers the bioequivalent alertness benefit of from about 10 mg to about 300 mg of caffeine.

The vitamin and mineral supplement can additionally comprise sweeteners, flavors, pharmaceutically acceptable carriers and excipients. The supplements can contain both vitamins and minerals.

Accordingly, the present invention provides vitamin stability due to the antioxidant benefits of the flavanols. When bracers, such as caffeine, and flavanols are both present in a vitamin and mineral supplement, alertness benefits are provided at the same time certain negative effects are minimized. The beneficial effects of flavanols are also provided.

DETAILED DESCRIPTION OF THE INVENTION

The present invention relates to nutritional supplements containing bracers and to supplements containing flavanols or green tea solids which give alertness benefits along with the beneficial effects of flavanols.

As used herein, the term "comprising" means various components can be conjointly employed in the nutritional supplements of this invention. Accordingly, the terms "consisting essentially of" and "consisting of" are embodied in the term comprising.

By "nutritional" or "nutritionally-supplemental amount" herein is meant that the supplements used in the practice of this invention provide a nourishing amount of vitamins and minerals. This supplemental amount will comprise at least 3% of the Recommended Dietary Allowance (RDA). Preferably, at least 10% of the RDA will be provided. The RDA for vitamins and minerals is as defined in The United States of America (see Recommended Daily Dietary Allowance-Food and Nutrition Board, National Academy of Sciences-National Research Council). This is supplemental or in addition to the amount found in the diet.

As used herein, the term "flavors" includes both fruit and botanical flavors.

As used herein the term "sweeteners" includes sugars, for example, glucose, sucrose, and fructose. Sugars also include high fructose corn syrup solids, invert sugar, sugar alcohols, including sorbitol, and mixtures thereof. Artificial sweeteners are also included in the term sweetener.

As used herein, a "pharmaceutical acceptable" component is one that is suitable for use with humans and/or animals without undue adverse side effects (such as toxicity, irritation, and allergic response) commensurate with a reasonable benefit/risk ratio. Further, as used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the duration of the treatment, the nature of concurrent therapy (if any), and the specific formulations employed.

As used herein the term "ephedra" is intended to encompass ephedrine, pseudoephedrine, and norpseudoephedrine obtained from the family Ephedracease, genus Ephedra and including the species sinica, vulgaris, nevadensis, antisiphylitica or other species.

As used herein the term "methylxanthine" is intended to encompass theobromine, theophylline and in particular, caffeine from natural sources such as Kola, cocoa nuts, coffee, mate' and teas, but also highly refined methylxanthines such as anhydrous powders, salts, derivatives, or mixtures thereof which are pharmaceutical acceptable and which are able to provide physiologic effects as described herein.

As used herein, the term "tea solids" refers to solids extracted from tea materials and which contain flavanols. Water can be used to extract tea solids from green tea which are then dried using suitable methods such as forced air drying, convection drying, oven drying, freeze drying or spray drying.

As used herein, the term "flavanols" refers to materials obtained from the genus Camellia including *Camellia sinensis* and *Camellia assaimica*, for instance, freshly gathered tea leaves, fresh tea leaves that are dried immediately after gathering, fresh tea leaves that have been heat treated before drying to inactivate any enzymes present, unfermented tea, fermented tea, instant green fermented tea, partially fermented tea leaves and aqueous extracts of these leaves. Tea materials are tea leaves, their extracts, tea plant stems, and other plant materials which are related. Members of the genus Phyllanthus, *Catechu gambir* or Uncaria family of tea plants can also be used. Mixtures of unfermented, partially fermented and fermented teas can be used.

MINERALS

The mineral supplement composition preferably comprises sources selected from calcium, phosphorus, magnesium, iron, zinc, iodine, selenium, copper, manganese, fluoride, chromium and molybdenum, sodium, potassium, and chloride. Additional minerals, though less preferred, include arsenic, nickel, silicon, boron, cadmium, lead, lithium, tin, vanadium, and cobalt. The minerals sources are preferably present in nutritionally relevant amounts, which means that the mineral sources used in the practice of this invention provide a nourishing amount of said minerals. Preferably, this amount comprises at least 3% of the RDA of these minerals, and more preferably, at least 10% of the RDA and most preferably at least 50% up to 500% of the RDA per unit dose of the finished supplement. Of course, it is recognized that the preferred daily intake of any mineral may vary with the user with greater than the RDA intakes being beneficial in some circumstances.

In general, the RDA for calcium will range from 400 mg for infants to 1200 mg for adults, depending somewhat on age. The RDA for phosphorus ranges from 300 mg to 1200 mg. The RDA for magnesium ranges from 40 mg to 400 mg. The RDA for iron ranges from 6 mg to 30 mg, depending somewhat on age and physiologic state. The RDA for zinc ranges from 5 mg to 19 mg. The RDA for iodine ranges for 40 ug to 200 ug. The RDA for selenium ranges from 10 ug to 75 ug. There are no specific RDA levels for copper, manganese, fluoride, chromium, and molybdenum. However a safe and adequate range for copper is from 0.4 mg to 3.0 mg depending;somewhat on age and an adequate range for manganese is 0.3 mg to 5.0 mg per day. A safe and adequate range for fluoride is 0.1 mg to 4.0 mg. A safe and adequate range from chromium is 10 ug to 200 ug. A safe and adequate range for molybdenum is 15 ug to 250 ug. There are no specific RDA levels for sodium, potassium, and chloride. Specific dietary allowances and estimated safe minimum requirements for arsenic, nickel, silicon, boron, cadmium, lead, lithium, tin, and vanadium have not been established in humans. However, there is evidence of their function in other mammals and thus, possibly for humans as well. For cobalt, the known nutritional function is as part of cyanocobalamin (vitamin B-12). The supplement composition comprising use of any of these latter minerals should employ levels known to be safe without risk of toxicity. Less preferred compositions would contain arsenic, lead, cadmium, and lithium.

The source of the mineral salt, both those with established RDA levels or with safe and adequate intake levels, as well as those with no as yet established human requirement, used in the practice of this invention can be any of the well known salts including carbonate, oxide, hydroxide, chloride, sulfate, phosphate, gluconate, lactate, acetate, fumarate, citrate, malate, amino acids and the like for the cationic minerals and sodium, potassium, calcium, magnesium and the like for the anionic minerals. However, the particular salt used and the level will depend upon their interaction with other supplement ingredients.

VITAMINS

The vitamin supplement composition preferably comprises sources selected from A, D, E, K, C (astorbit acid), thiamin, riboflavin, niacin, vitamin B-6, folate, vitamin B-12, biotin, and pantothenic acid. These vitamin sources are preferably present in nutritional relevant amounts, which means that the vitamin sources used in the practice of this invention provide a nourishing amount of said vitamins. Preferably, this amount comprises at least 3% of the RDA of the daily intake of said vitamin, more preferably at 10%, and most preferably at least 50% up to 1000% of the RDA per unit dose of the finished product. Of course, it is recognized that the preferred daily intake of any vitamin may vary with the user with greater than RDA intakes being beneficial in some circumstances.

In general, the RDA for vitamin A will range from about 1250 International Units (IU) to about 4330 IU depending somewhat on age and physiologic state. The RDA for vitamin D will range from about 200 IU to about 400 IU. The RDA for vitamin E will range from about 5 IU to about 18 IU. The RDA for vitamin K will range from 5 ug to 80 ug. The RDA of vitamin C will range from about 30 mg to about 95 mg. The RDA for thiamin will range from about 0.3 mg to about 1.6 mg. The RDA for riboflavin will range from about 0.4 mg to about 1.8 mg. The RDA for niacin will range from about 5 mg to about 20 mg. The RDA for vitamin B-6 will range from about 0.3 mg to about 2.2 mg. The RDA for folate will range from about 25 ug to about 400 ug. The RDA for vitamin B-12 will range from about 0.3 ug to about 2.6 ug. There are no specific RDA levels for biotin and pantothenic acid. However a safe and adequate range for biotin is from 10 μg to 100 μg and an adequate range for pantothenic acid is 2 mg to 7 mg.

Vitamin A precursors (provitamin A, carotenoids) can also be used including beta-carotene, alpha-carotene, cryptoxanthine and the like. The vitamin A esters and beta-carotene are highly preferred forms of vitamin A. Vitamin D can be selected from, for example, cholecalciferol (D3), ergocalciferol (D2), and their biologically active metabolites and precursors such as, 1-alpha-hydroxy vitamin D, 25-hydroxy vitamin D, 1,25-dihydroxy vitamin D and the like. Vitamin D as cholecalciferol is highly preferred. All-rac alpha-tocopherol and RRR-alpha-tocopherol and their esters are highly preferred as a source for vitamin E. Other sources of vitamin E include dl-alpha tocopherol (all -rac) and its esters such as acetate and the acid succinate, dl-alpha-tocopherol (RRR) and its esters, d-alpha-tocopherol and its esters, beta-tocopherol, gamma-tocopherol, and their esters, tocopheryl nicotinate, and the like. Vitamin K can be selected from phylloquinone (K1), menaquinone (K2), menadione and their salts and derivatives. Vitamin K1 is highly preferred. L-ascorbic acid is particularly preferred for the vitamin supplements of the present invention. However other forms of vitamin C, for example, L-ascorbic acid, D-ascorbic acid, DL-ascorbic acid, D-araboascorbic acid, dehydroascorbic acid, esters of ascorbic acid may also be used. The hydrochloride and nitrate salts of thiamin and thiamin alkyl disulfides such as the prophyidisulfide, tetrahydrofurfuryl disuifide, O-benzoyl disulfide can be used in the present invention. The hydrochloride and nitrate salts are highly preferred. The sources of riboflavin are selected, for example, from crystalline riboflavin coenzyme forms of riboflavin such as ravin adeninc dinucleotide, flavin adenine mononucleotide, riboflavin 5'-phosphate and their salts. Riboflavin is highly preferred. For niacin they comprise, for example, nicotinic acid, nicotinamide (niacinamide), the coenzyme forms of niacin such as nicotinamide adeninc dinucleotide, and nicotinamide adenine dinucleotide phosphate. Particularly preferred are nicotinamide and nicotinic acid. Vitamin B6 can be selected from hydrochloride salts or 5'-phosphates of pyridoxine, pyridoxamine, pyridoxal. The preferred vitamin B6 is pyridoxine hydrochloride. The folate can be in the form of folic acid, mono and polyglutamyl folates, dihydro and tetrahydro folates, methyl and formyl folates. Folic acid is a highly preferred form of folate. Sources of vitamin B-12 are, for example, cyanocobalamin, methylcobalamin, adenosylcobalamin, hydroxocobalamin and the like. Cyanocobalamin is highly preferred. Biotin for use in the vitamin and/or mineral supplements can be selected oxybiotin, biocytin, biotinol and the like. Biotin is highly preferred. For pantothenic acid the sources can be in the form of salts such as calcium pantothenate or as panthenol. Calcium pantothenate is a highly preferred source of pantothenic acid.

BRACERS

The bracers can be obtained from the extraction of a natural source or can be synthetically produced. The bracer is preferably present in physiologically relevant amounts, which means that the sources used in the practice of this invention provide a safe and effective quantity to achieve the desired benefit. The methylxanthines i.e. caffeine, theobromine and theophylline are well known bracers. However, numerous other xanthine derivatives have been isolated or synthesized. See, for example, Bruns, *Biochem. Pharmacol.*, 30, 325–333, (1981) describing more than one hundred purine bases structurally related heterocycles relative to xanthine. One or more of these compounds are present in the coffee bean, tea, kola nut, cacao pod, mate', yaupon, guarana paste and yoco. The most preferred methylxanthine is caffeine. Caffeine can be obtained from the aforementioned plants and their waste or else synthetically prepared. Preferably, the composition of the present invention contains from about 10 mg to 300 mg of caffeine or the bioequivalent amount of another methylxanthine or component source such as ephedra and the like. More preferably from about 30 mg to 200 mg of caffeine or the bioequivalent amount of 30 mg to 200 mg of caffeine, and most preferably the amount of caffeine is from about 50 mg to about 125 mg or equals the bioequivalent of from about 50 mg to 125 mg of caffeine. Of course, the actual amount of bracer added will depend on its alertness effect when compared to caffeine. The bioequivalent amount of bracer compared to caffeines is easily determined by one skilled in the art.

FLAVANOLS

The catechins and epicatechins are also known as flavanols. The flavanols can be obtained by extraction from any suitable plant. The flavanols can be extracted from either a single plant or mixtures of plants. Examples of the most common flavanols which are obtained from extraction from the tea plants and other members of the *catechu gambir* (or Uncaria family) are catechin, epicatechin, gallocatechin, epigallocatechin, *epicatechin gallate,* and *epigallocatechin gallate*. Derivatives of the flavanols can also be used in the practice of this invention including sugar salts, sugar esters, and other edible fruits, and other natural sources which also contain the flavanols but to a lesser extent. Any mixture of the flavanols can be used in the compositions of the present invention. Catechin is preferably used in combination with one of the other flavanols mentioned above. Particularly preferred are the unoxidized, unpolymerized flavanols. These flavanols can be extracted from green tea or other natural sources by any suitable method such as extraction with ethyl acetate or chlorinated solvents, see for example U.S. Pat. No. 4,935,256 to Tsai, 1990. The flavanols can also be prepared by synthetic or other appropriate chemical methods. Tea solids themselves can be the source of flavanols.

The amount of flavanols in the nutritional supplement can vary. Preferably at least 10 mg and more preferably from about 20 mg to 4000 mg of flavanols are used in the practice of this invention. Most preferably, from about 50 mg to 1000 mg is used per unit dose. When caffeine is part of the composition, the ratio of caffeine to flavanols in the supplement is from about 1:1 to about 1:30. Preferably the range is from about 1:1 to 1:10, and most preferably the range is from about 1:1.5 to 1:5.

ADDITIONAL INGREDIENTS

CARBOHYDRATES

The carbohydrates used in the preparation of the present invention usually include any of the ingestible mono or dissaccharidic materials, their hydrolysis products and mixtures thereof, well-known in the culinary arts. For example, glucose, sucrose and fructose, lactose, dextrose, maltose and galactose. Sugar alcohols can also be used in the compositions of the present invention. These sugar alcohols include sorbitol, mannitol, and xylitol.

In addition to sugar, the present invention can contain other natural or artificial sweeteners. Other suitable sweeteners include saccharin, cyclamates, acetosulfam, L-aspartyl-L-phenylalanine lower alkyl ester sweeteners (e.g. Aspartame), L-aspartyl-D-alanine amides (U.S. Pat. No. 4,411,925 to Brennan et al., 1983), L-aspartyl-D-serine amides (U.S. Pat. No. 4,3999,163 to Brennan et al., 1983), L-aspartyl-L-1-hydroxymethyl-alkaneamide sweeteners (U.S. Pat. No. 4,338,346 to Brand, 1092), L-aspartyl-1-hydroxy ethylalkaneamide sweeteners (U.S. Pat. No. 4,423,029 to Rizzi, 1983), L-aspartyl-D-phenylglycine ester and amide sweeteners (European Patent Application 168,112 to J. M. Janusz, published Jan. 15, 1986), and the like. A preferred sweetener is aspartame. Low calorie sweetener combinations containing a noncaloric sweetener such as aspartame and sugar, such as corn syrup solids, or sugar alcohols can be used in the compositions herein.

Other carbohydrates customary in tablets and powders, for example starches, modified starches and maltodextrins, can also be used in the preparations according to the present invention.

The amount of the sweetener effective in the supplements depends upon the particular sweetener used and the sweetness intensity desired. For noncaloric sweeteners, this amount varies depending upon the sweetness intensity of the particular sweetener. For sugar (i.e., sucrose), this amount can be from 1% to 85%. Typically from 10% to 50%, by weight sugar, is used. In determining the amount of sugar, any sugar or other sweetener present in the flavor component is also included. Low-calorie sweetener combinations containing a non caloric sweetener such as aspartame and a sugar, such as dextrose, or sugar alcohols can also be used in the supplements. The amount of sweetener(s) added to the supplement is within the skill of one in the art and depends on the sweetener intensity desired.

FLAVORS

If desired, the composition may contain a flavor component. The flavor component of the supplements may be selected from natural flavors, botanical flavors and mixtures thereof. The term "fruit flavor" refers to those flavors derived from the edible reproductive part of a seed plant, especially one having a sweet pulp associated with the seed. Also included within the term "fruit flavor" are synthetically prepared flavors made to simulate fruit flavors derived from natural sources. Fruit juice is also a fruit flavor as the term is used herein.

The term "botanical flavor" refers to flavors derived from parts of a plant other than fruit; i.e. derived from bean, nuts, bark, roots and leaves. Also included within the term "botanical flavor" are synthetically prepared flavors made to simulate botanical flavors derived from natural sources. Examples of such flavors include cocoa, chocolate, vanilla, coffee, tea, and peppermint. Botanical flavors can be derived from natural sources such as essential oils and extracts, or can be synthetically prepared.

The amount of the flavor component effective for imparting flavor characteristics to the supplements of the present invention ("flavor enhancing") depend on the flavor(s) selected, the flavor impression desired, the form of the supplement and the form of the flavor component. The amount of flavor(s) added to the supplement is within the skill of one in the art and depends on the flavor intensity desired.

SUPPLEMENTAL FORMS

The vitamins, minerals, bracers, and/or flavanols are preferably coadministered in the form of a tablet or capsule, as an agglomerated powder or in a liquid form. Capsule or tablet containing vitamins and minerals together or alone with the bracers and/or flavanols can be formulated and are easy to swallow or chew.

Solid forms include tablets, capsules, granules, and bulk powders. The dry forms of the supplements are typically taken in conjunction with water or diluted with water. When diluted with water this factor must be considered when preparing the mix. Tablets may contain suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules and effervescent preparations reconstituted from effervescent granules. Such liquid oral dosage forms may contain, for example, suitable solvents, preservatives, emulsifying agents, suspending agents, diluents, sweeteners, melting agents, and coloring and flavoring agents.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described in the following references: 7 *Modem Pharmaceutics,* Chapters 9 and 10 (Banker & Rhodes, Editors, 1979); Lieberman et al., *Pharmaceutical Dosage Forms: Tablets* (1981); and Ansel, *Introduction to Pharmaceutical Dosage Forms* 2nd Edition (1976).

METHOD FOR PREPARING COMPOSITION

The following examples are illustrative and are not meant to be limiting to the invention.

EXAMPLE I

A swallowable multivitamin plus mineral supplement containing caffeine and flavanols is prepared as follows.

| Component | Amount (grams) |
| --- | --- |
| 1. Cupric Oxide | 16.4 |
| 2. Zinc Oxide | 136.4 |
| 3. Manganese Acetate | 69.0 |
| 4. Ferrous Sulfate | 198.7 |
| 5. Chromic Chloride | 0.7 |
| 6. Spray Dried Green Tea Powder (6.86% Caffeine and 17.41% Flavanols) | 6388.0 |
| 7. Ascorbic Acid | 438.2 |
| 8. Thiamin Mononitrate | 11.0 |
| 9. Riboflavin | 12.4 |
| 10. Niacinamide | 146.1 |
| 11. Pyridoxine Hydrochloride | 17.7 |
| 12. Cyanocobalamin | 0.037 |
| 13. Calcium Pantothenate | 55.9 |
| 14. Beta-Carotene | 21.9 |
| 15. Calcium Carbonate | 2191.0 |
| 16. Croscarmelose | 1378.0 |
| 17. Magnesium Stearate | 292.2 |
| 18. Silicone Dioxide | 146.1 |

A. Mineral and Green Tea Premix

1. Add items #1, 2, 3, 4, 5, 6, and 15 into a suitable blender and mix for ten minutes or until uniform blend is obtained.

B. Vitamin Premix

1. Add items #8, 9, and 13 into a suitable blender and mix for five minutes. Screen or mill through 30 mesh.

2. Add items # 7, 10, 11, 12, and 14 into a suitable blender and mix for five minutes.

3. Add Step 1 and Step 2 and mix for additional 10 minutes or until uniform blend is obtained.

C. Final Blend and Compression

1. Add the mineral premix, the vitamin premix, and items 16, 17, and 18 into a suitable blender and mix for fifteen minutes or until a uniform blend is obtained.

2. Compress the final blend on suitable rotary tablet press equipped with capsule shape tooling. Core tablets weigh approximately 1400 mg and contain the following:

| Ingredient | Amount |
| --- | --- |
| Vitamin A (as beta-carotene) | 1680 IU |
| Vitamin C | 60 mg |

-continued

| Ingredient | Amount |
| --- | --- |
| Thiamin | 1.5 mg |
| Riboflavin | 1.7 mg |
| Niacin | 20 mg |
| Vitamin B-6 | 2 mg |
| Pantothenic Acid | 7 mg |
| Calcium | 120 mg |
| Zinc | 15 mg |
| Iron | 10 mg |
| Copper | 2 mg |
| Manganese | 3 mg |
| Chromium | 100 ug |
| Caffeine | 60 mg |
| Flavanols | 152 mg |

AQUEOUS FILM COATING OF COMPRESSED TABLETS

| A. | Coating Solution | % Used |
| --- | --- | --- |
| 1. | Hydroxyproplymethyl Cellulose | 7.50 |
| 2. | Polyethylene Glycol 8000 | 0.94 |
| 3. | Opaspray Color White | 7.13 |
| 5. | Purified Water | 84.43 |

B. Preparation

1. Using high agitation, thoroughly disperse the hydroxypropylmethyl cellulose and PEG 8000 in purified water until a clear dispersion is obtained.

2. Add Opaspray and disperse gently to obtain homogeneous color suspension.

Coating Procedure

1. Prewarm core tablets in 24" pan coater rotating at 14 rpm.

2. Spray coating suspension continuously at a rate of 45 grams per minute with inlet air set at 80° C. and exhaust temperature ranging 58° C. to 60° C.

3. Coat tablet cores until weight gain is 4%.

This supplement supplies a useful quantity of several vitamins and minerals in a matrix that yields the positive alertness effects of a bracer while moderating its negative effects. It is most appropriately consumed by individuals who wish to improve their nutritional status and are somewhat sensitive to the negative effects of caffeine.

EXAMPLE II

A swallowable multivitamin supplement containing caffeine and flavanols is prepared by omitting components #1–5 and 15 in example I above and reducing the final core tablet weight to approximately 1080 mg.

EXAMPLE III

A swallowable multimineral supplement containing caffeine and flavanols is prepared by omitting components #7–14 in example I above and reducing the final core tablet weight to approximately 1315 mg.

EXAMPLE IV

A swallowable multivitamin plus minerals supplement containing caffeine is prepared by replacing component #6 from example I above with 100 mg of caffeine and reducing the final core tablet weight to approximately 625 mg.

EXAMPLE V

Multimineral chewable lozenges with caffeine are prepared comprising:

| | Component | Amount (grams) |
| --- | --- | --- |
| 1. | Cupric Gluconate | 7.14 |
| 2. | Zinc Formate | 9.51 |
| 3. | Manganese Sulfate | 4.67 |
| 4. | Ferrous Fumarate | 15.2 |
| 5. | Chromic Formate | 0.241 |
| 6. | Caffeine (anhydrous) | 80.0 |
| 7. | Calcium Phosphate Dibasic | 906.3 |
| 8. | Magnesium Oxide | 154.7 |
| 9. | Potassium Iodide | 0.065 |
| 10. | Sodium Selenate | 0.044 |
| 11. | Sodium Molybdate | 0.178 |
| 12. | Citric Acid | 50.00 |
| 13. | Granulated Crystalline Mannitol | 2000.0 |
| 14. | Magnesium Stearate | 15.0 |
| 15. | Silicone Dioxide | 7.0 |
| 16. | Fruit Flavor | 6.0 |

Copper, Zinc and Iron may be obtained in coated form from the supplier in order to reduce off flavors.

Blending and Compression

1. Add item numbers 1 through 13, and 16 into a suitable blender and mix for 15 minutes or until a uniform blend is obtained.

2. Add items 14 and 15 and mix ten minutes.

3. Compress the blended material on suitable rotary tablet press equipped with round shape tooling. Tablet target weight is approximately 3,256 mg with a hardness range of 13–19 SCU.

When this tablet composition is taken 3 times per day it supplies 100% of the RDA of the above listed minerals for an adult women. In addition, the individual consuming the supplement experiences the alertness effects of caffeine and the need to consume coffee is eliminated.

EXAMPLE VI

A swallowable multivitamin plus minerals supplement containing flavanols in a hard gelatin capsule dosage form is prepared as follows.

| | Ingredients | |
| --- | --- | --- |
| | Component | Amount (grams) |
| 1. | Cupric Oxide | 16.4 |
| 2. | Zinc Oxide | 136.4 |
| 3. | Manganese Acetate | 69.0 |
| 4. | Ferrous Sulfate | 198.7 |
| 5. | Chromic Chloride | 0.7 |
| 6. | *Purified Green Tea Powder (5.0% Caffeine and 95.0% Flavanols) | 6388.0 |
| 7. | Ascorbic Acid | 438.2 |
| 8. | Thiamin Mononitrate | 11.0 |
| 9. | Riboflavin | 12.4 |
| 10. | Niacinamide | 146.1 |
| 11. | Pyridoxine Hydrochloride | 17.7 |

| Ingredients | |
|---|---|
| Component | Amount (grams) |
| 12. Cyanocobalamin | 0.037 |
| 13. Calcium Pantothenate | 55.9 |
| 14. Beta-Carotene | 21.9 |
| 15. Calcium Carbonate | 2191.0 |
| 16. Avicel PH101 | 6653.85 |
| 17. Magnesium Stearate | 292.2 |
| 18. Silicone Dioxide | 146.1 |

*The purified green tea powder is obtained according to the method of Tsai (U.S. Pat. No. 4,935,256).

A. Mineral and Flavanol Premix

1. Add items #1, 2, 3, 4, 5, 6, and 15 into a suitable blender and mix for ten minutes or until uniform blend is obtained.

B. Vitamin Premix

1. Add items #8, 9, and 13 into a suitable blender and mix for five minutes. Screen or mill through 30 mesh.

2. Add items # 7, 10, 11, 12, and 14 into a suitable blender and mix for five minutes.

3. Add Step 1 and Step 2 and mix for additional 10 minutes or until uniform blend is obtained.

C. Final Blend and Encapsulation

1. Add the mineral premix, the vitamin premix and items 16, 17, and 18 into a suitable blender and mix for fifteen minutes or until a uniform blend is obtained.

2. Capsule fill the final blend on suitable automatic capsule filler. Target weight is 700 mg per size O capsule resulting in two capsules being required per dose. Banding or liquid-sealing is recommended to ensure tamper resistance.

This supplement provides a nourishing amount of several vitamins and minerals in a matrix which delivers the beneficial effects of flavanols. It is useful for those seeking to improve the diet through supplementation with a physiological feedback and who desire to avoid caffeine.

EXAMPLE VII

A swallowable multivitamin supplement containing flavanols is prepared by omitting components # 1–5 and 15 in example VI above and reducing the final target capsule weight to approximately 540 mg.

EXAMPLE VIII

A swallowable multimineral supplement containing flavanols is prepared by omitting components # 7–14 in example VI above and reducing the final target capsule weight to approximately 660 mg.

EXAMPLE IX

A swallowable multivitamin plus minerals supplement containing caffeine and flavanols in a soft gelatin capsule dosage form is prepared as follows.

| Ingredients | |
|---|---|
| *Component | Amount (grams) |
| Cupric Oxide | 16.4 |
| Zinc Oxide | 136.4 |
| Manganese Acetate | 69.0 |
| Ferrous Sulfate | 198.7 |
| Chromic Chloride | 0.7 |
| Spray Dried Green Tea Powder (6.86% Caffeine and 17.41% Flavanols) | 6388.0 |
| Ascorbic Acid | 438.2 |
| Thiamin Mononitrate | 11.0 |
| Riboflavin | 12.4 |
| Niacinamide | 146.1 |
| Pyridoxine Hydrochloride | 17.7 |
| Cyanocobalamin | 0.037 |
| Calcium Pantothenate | 55.9 |
| Beta-Carotene | 21.9 |
| Calcium Carbonate | 2191.0 |
| Vegetable Oil | 9,704.0 |

*All suspended ingredients must be reduced to a particle size of less than 80 mesh.

A. Blending Process

1. Add the vegetable oil to a suitable high shear mixer and begin agitation.

2. Sequentially add remaining components and continue mixing until a homogeneous mixture is obtained.

B. Soft Gelatin Encapsulation

1. Transfer mixture to filler tank of suitable rotary die soft gelatin encapsulator. Mixture is under constant agitation in order to prevent settling of suspension.

2. Capsules are formed with approximately 1400 mg of mixture fill, then washed, dried, and cured in an appropriate manner. Two capsules are required to provide one dose of multivitamin plus minerals containing caffeine and flavanols.

This encapsulated mixture provides a nutritionally supplemental amount of several vitamins and minerals for those seeking to improve the diet in a matrix that provides the physiologically positive alertness effects of a bracer along with the moderating effects of flavanols.

EXAMPLE X

Multivitamin supplement containing caffeine in liquid form is prepared as follows.

| Component | Amount (grams) | % RDA/Dose |
|---|---|---|
| Vitamin A | 2.75 | 100 |
| Vitamin D | 0.01 | 100 |
| Vitamin C | 200 | 333 |
| Thiamine | 10.0 | 667 |
| Riboflavin | 10.0 | 588 |
| Niacin | 100.0 | 500 |
| Vitamin B6 | 4.1 | 205 |
| Vitamin B12 | 0.005 | 83 |
| Pantothenic Acid | 21.4 | 214 |
| Purified Water | 4,348.0 | |
| Caffeine | 100.0 | |
| Sucrose | 200 | |
| Fruit Flavor | 3.0 | |
| Preservatives | 1.0 | |

A. Blending Process

1. Add the purified water to a suitable high shear mixer and begin agitation.

2. Sequentially add remaining components and continue mixing until a solution is obtained. Each 5 ml (one teaspoon) delivers one dose.

This liquid supplement is useful for improving the diet via consumption of several vitamins. Furthermore, it provides the physiologically positive alertness effects of caffeine in a matrix appropriate for those who have difficulty taking tablet type dose forms.

What is claimed:

1. A vitamin supplement comprising:
   (a) from about 3% to about 1000% of the RDA of vitamins;
   (b) from about 10 mg to about 4000 mg flavanols; and
   (c) a bracer, wherein said bracer delivers the bioequivalent alertness benefit of from about 10 mg to about 300 mg of caffeine.

2. A supplement according to claim 1 further comprising from about 1% to about 85% by weight carbohydrate.

3. A supplement according to claim 2 wherein said vitamin content is from about 10% to about 150% of the RDA of vitamins.

4. A supplement according to claim 3 wherein said vitamins are selected from vitamin A, D, E, K, C, thiamin, riboflavin, niacin, vitamin B-6, folate, vitamin B-12, biotin, pantothenic acid and mixtures thereof.

5. A supplement according to claim 4 wherein said bracer delivers the bioequivalent alertness benefit of from about 30 mg to about 200 mg of caffeine.

6. A supplement according to claim 5 wherein said bracer delivers the bioequivalent alertness benefit of from about 50 mg to about 125 mg of caffeine.

7. A supplement according to claim 6 wherein said bracer is caffeine.

8. A supplement according to claim 7 wherein the ratio of caffeine to flavanols is from about 1:1.5 to about 1:5.

9. A mineral supplement comprising:
   (a) from about 3% to about 500% of the RDA of minerals; and
   (b) from about 10 mg to about 4000 mg flavanols.

10. A supplement according to claim 9 further comprising a bracer wherein said bracer delivers the bioequivalent alertness benefit of from about 10 mg to about 300 mg of caffeine.

11. A supplement according to claim 10 further comprising from about 1% to about 85% by weight carbohydrate.

12. A supplement according to claim 11 wherein said minerals are selected from calcium, phosphorus, magnesium, iron, zinc, iodine, selenium, copper, maganese, fluoride, chromium, molybdenum, sodium, potassium, chloride and mixtures thereof.

13. A supplement according to claim 12 wherein said bracer delivers the bioequivalent amount of from about 50 mg to about 125 mg of caffeine.

14. A supplement according to claim 13 wherein said bracer is caffeine.

15. A supplement according to claim 14 wherein the ratio of caffeine to flavanols is from about 1:1.5 to about 1:5.

16. A vitamin and mineral supplement comprising:
    (a) from about 3% to about 1000% of the RDA of vitamins;
    (b) from about 3% to about 500% of the RDA of minerals; and
    (c) from about 10 mg to about 4000 mg flavanols.

17. A supplement according to claim 16 further comprising a bracer wherein said bracer delivers the bioequivalent alertness benefit of from about 10 mg to about 300 mg of caffeine.

18. A supplement according to claim 17 further comprising from about 1% to about 85% by weight carbohydrate.

19. A supplement according to claim 18 wherein said vitamins are selected from vitamin A, D, E, K, C, thiamin, riboflavin, niacin, vitamin B-6, folate, vitamin B-12, biotin, pantothenic acid and mixtures thereof; and said minerals are selected from calcium, phosphorus, magnesium, iron, zinc, iodine, selenium, copper, manganese, fluoride, chromium, molybdenum, sodium, potassium, chloride and mixtures thereof.

20. A supplement according to claim 19 wherein said bracer delivers the bioequivalent alertness benefit of from about 30 mg to about 200 mg of caffeine.

21. A supplement according to claim 20 wherein said bracer delivers the bioequivalent alertness benefit of from about 50 mg to about 125 mg of caffeine.

22. A supplement according to claim 21 wherein said bracer is caffeine.

23. A supplement according to claim 22 wherein the ratio of caffeine to flavanols is from about 1:1 to about 1:10.

24. A supplement according to claim 23 wherein the ratio of caffeine to flavanols is from about 1:1.5 to about 1:5.

* * * * *